United States Patent
Viksoe-Nielsen et al.

(10) Patent No.: US 7,943,336 B2
(45) Date of Patent: May 17, 2011

(54) CUTINASE FOR DETOXIFICATION OF FEED PRODUCTS

(75) Inventors: Anders Viksoe-Nielsen, Slangerup (DK); Birthe Hauerbach Soerensen, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 63 days.

(21) Appl. No.: 12/339,541

(22) Filed: Dec. 19, 2008

(65) Prior Publication Data

US 2009/0162480 A1 Jun. 25, 2009

(30) Foreign Application Priority Data

Dec. 20, 2007 (EP) .................................... 07150205

(51) Int. Cl.
*C12Q 1/34* (2006.01)

(52) U.S. Cl. ........................ 435/18; 435/195; 435/197

(58) Field of Classification Search ................. 435/197, 435/18, 195
See application file for complete search history.

(56) References Cited

U.S. PATENT DOCUMENTS

2003/0073239 A1 4/2003 Karlovsky et al.

FOREIGN PATENT DOCUMENTS

| CA | 2192983 | 9/1999 |
| EP | 0981953 | 3/2000 |
| WO | WO 2007/133263 | 11/2007 |

OTHER PUBLICATIONS

Brodhagen et al., Molecular Plant Pathology, vol. 7, No. 4, pp. 285-301 (2006).

*Primary Examiner* — Tekchand Saidha
(74) *Attorney, Agent, or Firm* — Elias Lambiris

(57) ABSTRACT

The present invention relates to a method comprising treatment with cutinase for detoxification of feed products contaminated by the mycotoxin zearalenone.

16 Claims, No Drawings

US 7,943,336 B2

CUTINASE FOR DETOXIFICATION OF FEED PRODUCTS

CROSS-REFERENCE TO RELATED APPLICATIONS

This application is claims priority or the benefit under 35 U.S.C. 119 of European application no. 07150205.8 filed Dec. 20, 2007. The contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to a method comprising treatment with cutinase for detoxification of feed products contaminated by the mycotoxin zearalenone.

BACKGROUND OF THE INVENTION

Several plant pathogenic and/or post-harvest *Fusarium* species on cereals produce toxic substances of considerable concern to livestock and poultry producers, e.g., deoxynivalenol, T-2 toxin, HT-2 toxin, diacetoxyscirpenol and zearalenone.

Zearalenone is found worldwide in a number of cereal crops, such as maize, barley, oats, wheat, rye, rice, millet and sorghum. Zearalenone production does not seem to occur in significant amounts prior to harvest, but under proper environmental conditions, it is readily produced on corn and small grains in storage.

When cereal grain is used in ethanol production and the starch is consumed the zearalenone is concentrated in the fermentation by-products, e.g., in the distiller's dried grain. The contents of zearalenone in the fermentation by-products may be increased three-fold relative to the cereal grain.

The toxin is heat-stable, and it is not destroyed by long storage, roasting, or by the addition of propionic acid or mold retardants.

Despite their structural dissimilarity to the steriodal estrogens, zearalenone and several of its derivatives possess estrogenic activity. Zearalenone undergoes a folding such that hydroxyl or potential hydroxyl groups become appropriately orientated to facilitate binding to tissue receptors that normally bind estrogens.

Zearalenone is the primary toxin causing infertility, abortion or other breeding problems, especially in swine. The symptoms are especially severe in prepubertal gilts including enlarged mammae, swelling of uterus and vulva, and atrophy of the ovaries. In severe cases, prolapse of the vulva and rectum may occur. Boars exhibit enlarged mammae and atrophied testes.

Zearalenone is present in the meat from animals feeding on contaminated grain as well as in bread baked from contaminated wheat. While cases of poisoning of humans are rare there is concern about the effect of the long term exposure of humans to such an estrogenic activity.

Inactivation of mycotoxins, including zearalenone, using epoxidase or lactonase is disclosed in WO 96/12414.

There is a need for further methods of detoxification of animal feed products, e.g., such as fermentation by-products, including distiller's wet and dried grain, contaminated by the mycotoxin zearalenone.

SUMMARY OF THE INVENTION

The inventors of the present invention have discovered that zearalenone in a feed product can be degraded by treating the feed product with a cutinase. Accordingly, in a first aspect the invention provides a process for degrading zearalenone in a feed product which process comprises treating said feed product with a cutinase.

In a second aspect the invention provides a use of a cutinase for degrading a mycotoxin.

DETAILED DESCRIPTION OF THE INVENTION

Zearalenone

In the context of this invention the term "zearalenone" comprises the mycotoxin zearalenone produced from certain *Fusarium* sp. The IUPAC name is (4S, 12E)-15, 17-Dihydroxy-4methyl-3oxabicyclo[12.4.0]octadeca-12, 15, 17, 19tetraene-2, 8-dione. The term "zearalenone" also comprises any derivative of zearalenone which comprises an internal carboxylic ester bond susceptible for modification by a cutinase.

Animal Feed Products

The term "animal" includes all animals, including human beings. Examples of animals are cattle, (including but not limited to cows and calves); mono-gastric animals, e.g., pigs or swine (including, but not limited to, piglets, growing pigs, and sows); poultry such as turkeys and chicken (including but not limited to broiler chicks, layers); and fish (including but not limited to salmon).

The term "feed" or "feed product" means any compound, preparation, mixture, or composition suitable for, or intended for intake by an animal.

The feed product may be a product which apart from an unwanted level of zearalenone is suitable for consumption by an animal. The feed product can also be a product suspected of comprising an unwanted level of zearalenone, and/or a product having an unknown level of zearalenone, including products not comprising a detectable level of zearalenone.

Preferably the feed product is a grain based product. Preferably the grain based product comprises cereal(s), e.g., one or more of corn, wheat, barley, rye, rice, sorghum and millet. Also preferred are grain based product comprising material derived from one or more of corn, wheat, barley, rye, rice, sorghum and millet. In one embodiment, the feed product may, e.g., be derived solely from cereal(s), and in another embodiment partly from legumes, e.g., from soybean, and partly from cereals. The grain based product may comprise whole or milled grain, e.g., wet or dry milled grain, including grain based product comprising fractions of wet or dry milled grain, e.g., gluten, protein, starch, and/or oil fractions. Also preferred are products comprising a by-product from brewing and/or fermentation processes, e.g., spent grain. Spent grain is the by-products from the production of alcoholic beverages and ethanol fuels. Brewers' spent grain (BSG) is the residue of beer making in breweries, which use malted barley as the major raw material. Distiller's spent grain (DSG) is the product left in distilleries after alcohol is removed by distillation from the fermented grains such as corn, wheat, barley, rice, and rye. Distiller's spent grain is also known as distiller's grain. Wet distiller's grain (WDG) is dried to produce dried distiller's grain (DDG) which is used primarily as animal feed.

Cutinases

In the context of this invention the term "cutinases" include enzymes comprised by the enzyme classification E.C.3.1.1.74. Preferred are the below mentioned enzymes as well as enzymes with homologous sequence, especially recombinant and/or substantially purified enzymes.

The cutinase may be derived from a fungus. Particularly, the cutinase may be derived from a strain of *Humicola*, particularly *H. insolens*, more particularly *H. insolens* strain DSM1800 (U.S. Pat. No. 5,827,719) or from a strain of *Fusarium*, e.g., *F. roseum culmorum*, or particularly *F. solani pisi* (WO 90/09446; WO 94/14964, WO 94/03578). The fungal cutinase may also be derived from a strain of *Rhizoctonia*, e.g., *R. solani*, or a strain of *Altemaria*, e.g., *A. brassicicola* (WO 94/03578). The cutinase may also be a variant of a parent cutinase such as those described in WO 00/34450, or WO 01/92502, all of which are hereby incorporated by reference. The cutinase may be the variant of the *Humicola insolens* cutinase comprising the substitutions E6Q, G8D, A14P, N15D, E47K, S48E, R51P, A88H, A91H, A130V, E179Q and R189V, which is disclosed at p. 24, line 11 of WO 2001/092502.

SEQ ID NO: 1 is the amino acid sequence of the *Humicola insolens* cutinase (corresponding to the mature part of SEQ ID NO: 2 of U.S. Pat. No. 5,827,719, and of SEQ ID NO: 1 of WO 01/92502), and SEQ ID NO: 2 is the amino acid sequence of the *Fusarium solani pisi* according to FIG. 1D of WO 94/14964.

The cutinase must be present in the medium to be detoxified in effective amounts. Preferably the cutinase is present in concentrations of 0.01-100 mg enzyme protein per kg dry matter, preferably 0.1-10 mg enzyme protein per kg dry matter, or more preferably 1-5 mg enzyme protein per kg dry matter.

The Medium

In an embodiment the cutinase is degrading the zearalenone in a medium comprising the feed product. The medium is preferably aqueous and may be a liquid, a paste or a slurry. To form a suitable medium water may be added to the feed product. The cutinase be comprised in solid or liquid formulations suitable for application to said medium.

In a embodiment the cutinase is degrading the zearalenone to an extent whereby the content of zearalenone per kg dry matter feed product is reduced to less than 50%, preferably less than 60%, more preferably less than 70%, and most preferably to less than 80% of the initial amount.

The detoxifixation efficiency of the invention depends on, e.g., availability of water, pH, temperature and buffer of the medium. For example, the treatment may take place at a pH-value at which the relative activity of the actual cutinase is at least 50, or 60, or 70, or 80 or 90%. Likewise, for example, the treatment may take place at a temperature at which the relative activity of the actual cutinase is at least 50, or 60, or 70, or 80 or 90%. The relative activity is calculated relative to the activity at the pH value where the highest activity is observed.

pH in the Medium

Depending, inter alia, on the characteristics of the cutinase employed, the pH in the medium employed should normally be in the range of 5-11, preferably in the range 6-10, e.g., 6.5-8.5.

Temperature in the Medium

Preferably a reaction temperature is applied which is dose to the optimum temperature for the cutinase. In numerous embodiments of the invention, temperatures in the range of 10-65° C., more preferably 30-50° C., should be employed.

Treatment Duration

The duration of treatment depends, inter alia, on the treatment type, the type of item to be treated, the properties of the medium, e.g., temperature and pH and the type and amounts of enzyme employed.

The enzymatic reaction is continued until the desired result is achieved, following which it may or may not be stopped by inactivating the enzyme, e.g., by a heat-treatment step.

For detoxification purposes treatment times in the range of 1 minute to 1 week may be employed. In many cases a treatment time in the range of 6 to 48 hours will be suitable.

Identity

The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous Sequence

The term "homologous sequence" is defined as a predicted protein that gives an E value (or expectancy score) of less than 0.001 in a tfasty search (Pearson, W.R., 1999, in *Bioinformatics Methods and Protocols*, S. Misener and S. A. Krawetz, ed., pp. 185-219) with a specified sequence.

The term "homologous sequence" may also be defined as a sequence that has a degree of identity at least 75%, at least 80%, at least 85%, at least 90%, at least 95%, at least 97%, at least 98%, at least 99%, or even 100%, to a specified sequence.

EXAMPLES

Example 1

Enzyme: A recombinantly produced enzyme composition comprising the variant of the cutinase from *Humicola insolens* disclosed at p. 24, line 11 of WO 2001/092502.

Assay: Reactions were performed in 300 microL volumes in eppendorf tubes comprising zearalenone 30 microM, Tris 100 mM and enzyme 0.1 mg EP/mL. In control reactions the enzyme volume was substituted an equivalent amount of H$_2$O. The reactions were incubate 24 hours at 37° C. before being terminated by adding 600 microL of a 100 microM acetonitrile stop solution. Reactions were stored at −20° C. until chromatographic analysis.

Chromatographic analysis: Samples were centrifugated and the supernatant analysed for zearalenone by HPLC-DAD as described by Smedsgaard (*J. Chromatogr. A*, 1997, 760: 264-270). The DAD scanned from 200-600 nm. Separation was done on a Phenomenex (Torrance, Calif.) Luna C18(2) 10×2 mm ID, 3 micrometer, column 2, using a linear gradient moving form 5% to 100% acetonitrile in 20 min. Residual zearalenone was calculated relative to the control. The results are presented in Table 1.

TABLE 1

Residual zearalenone after 24 hours incubation with or without a cutinase at pH 7.

| Enzyme | Residual zearalenone (%) |
| --- | --- |
| Control | 100 |
| Cutinase | 19 |

The invention claimed is:

1. A process for degrading zearalenone in a feed product which process comprises treating said feed product with a cutinase in a medium, wherein the dosage of the cutinase is 0.01-100 mg enzyme protein per kg dry matter.

2. The process of claim 1, wherein the dosage of the cutinase is 0.1-10 mg enzyme protein per kg dry matter.

3. The process of claim 1, wherein the dosage of the cutinase is 1-5 mg enzyme protein per kg dry matter.

4. The process of claim 1, wherein the feed product is a grain based feed product.

5. The process of claim 1, wherein the feed product comprise one or more selected from the group consisting of corn, wheat, barley, rye, rice, sorghum and millet.

6. The process of claim 1, wherein the feed product is an animal feed composition.

7. The process of claim 1, wherein the feed product is a by-product from a fermentation process.

8. The process of claim 1, wherein the feed product comprises brewer's spent grain, distiller's spent grain, distiller's wet grain, and/or distiller's dried grain.

9. The process of claim 1, wherein the feed product is a swine feed product.

10. The process of claim 1, wherein the cutinase has at least 95% sequence identity to SEQ ID NO: 1.

11. The process of claim 1, wherein the cutinase comprises the sequence of SEQ ID NO: 1.

12. The process of claim 10, wherein the cutinase is a variant of the cutinase shown in SEQ ID NO: 1 comprising one or more substitutions selected from the group consisting of G8D, N15D, S48E, A88H, N91H, A130V and R189V, wherein the variant has at least 95% sequence identity to SEQ ID NO: 1.

13. The process of claim 1, wherein the cutinase has at least 95% sequence identity to SEQ ID NO: 2.

14. The process of claim 1, wherein the cutinase comprises the sequence of SEQ ID NO: 2.

15. The process of claim 1, wherein the medium as a pH in the range of 5-11.

16. The process of claim 1, wherein the feed product is treated with a cutinase at a temperature of 10-65° C.

* * * * *

SEQUENCE LISTING

<160> NUMBER OF SEQ ID NOS: 2

<210> SEQ ID NO 1
<211> LENGTH: 194
<212> TYPE: PRT
<213> ORGANISM: Humicola insolens
<220> FEATURE:
<221> NAME/KEY: mat_peptide
<222> LOCATION: (1)..(194)

<400> SEQUENCE: 1

```
Gln Leu Gly Ala Ile Glu Asn Gly Leu Glu Ser Gly Ser Ala Asn Ala
1               5                   10                  15

Cys Pro Asp Ala Ile Leu Ile Phe Ala Arg Gly Ser Thr Glu Pro Gly
                20                  25                  30

Asn Met Gly Ile Thr Val Gly Pro Ala Leu Ala Asn Gly Leu Glu Ser
            35                  40                  45

His Ile Arg Asn Ile Trp Ile Gln Gly Val Gly Gly Pro Tyr Asp Ala
        50                  55                  60

Ala Leu Ala Thr Asn Phe Leu Pro Arg Gly Thr Ser Gln Ala Asn Ile
65                  70                  75                  80

Asp Glu Gly Lys Arg Leu Phe Ala Leu Ala Asn Gln Lys Cys Pro Asn
                85                  90                  95

Thr Pro Val Val Ala Gly Gly Tyr Ser Gln Gly Ala Ala Leu Ile Ala
            100                 105                 110

Ala Ala Val Ser Glu Leu Ser Gly Ala Val Lys Glu Gln Val Lys Gly
        115                 120                 125

Val Ala Leu Phe Gly Tyr Thr Gln Asn Leu Gln Asn Arg Gly Gly Ile
    130                 135                 140

Pro Asn Tyr Pro Arg Glu Arg Thr Lys Val Phe Cys Asn Val Gly Asp
145                 150                 155                 160

Ala Val Cys Thr Gly Thr Leu Ile Ile Thr Pro Ala His Leu Ser Tyr
                165                 170                 175

Thr Ile Glu Ala Arg Gly Glu Ala Ala Arg Phe Leu Arg Asp Arg Ile
            180                 185                 190

Arg Ala
```

<210> SEQ ID NO 2
<211> LENGTH: 199
<212> TYPE: PRT
<213> ORGANISM: Fusarium solani pisi
<220> FEATURE:
<221> NAME/KEY: mat_peptide
<222> LOCATION: (1)..(199)

-continued

```
<400> SEQUENCE: 2

Gly Arg Thr Thr Arg Asp Asp Leu Ile Asn Gly Asn Ser Ala Ser Cys
1               5                   10                  15

Ala Asp Val Ile Phe Ile Tyr Ala Arg Gly Ser Thr Glu Thr Gly Asn
            20                  25                  30

Leu Gly Thr Leu Gly Pro Ser Ile Ala Ser Asn Leu Glu Ser Ala Phe
        35                  40                  45

Gly Lys Asp Gly Val Trp Ile Gln Gly Val Gly Gly Ala Tyr Arg Ala
    50                  55                  60

Thr Leu Gly Asp Asn Ala Leu Pro Arg Gly Thr Ser Ser Ala Ala Ile
65                  70                  75                  80

Arg Glu Met Leu Gly Leu Phe Gln Gln Ala Asn Thr Lys Cys Pro Asp
                85                  90                  95

Ala Thr Leu Ile Ala Gly Gly Tyr Ser Gln Gly Ala Ala Leu Ala Ala
            100                 105                 110

Ala Ser Ile Glu Asp Leu Asp Ser Ala Ile Arg Asp Lys Ile Ala Gly
            115                 120                 125

Thr Val Leu Phe Gly Tyr Thr Lys Asn Leu Gln Asn Arg Gly Arg Ile
130                 135                 140

Pro Asn Tyr Pro Ala Asp Arg Thr Lys Val Phe Cys Asn Thr Gly Asp
145                 150                 155                 160

Leu Val Cys Thr Gly Ser Leu Ile Val Ala Ala Pro His Leu Ala Tyr
            165                 170                 175

Gly Pro Asp Ala Arg Gly Pro Ala Pro Glu Phe Leu Ile Glu Lys Val
            180                 185                 190

Arg Ala Val Arg Gly Ser Ala
            195
```